United States Patent [19]

Petersen et al.

[11] Patent Number: 4,851,160
[45] Date of Patent: Jul. 25, 1989

[54] PROCESS FOR THE PREPARATION OF BENZOIC ACID DERIVATIVES

[75] Inventors: Uwe Petersen, Leverkusen; Michael Schriewer, Odenthal; Ernst Kysela, Bergisch-Gladbach; Klaus Grohe, Odenthal, all of Fed. Rep. of Germany

[73] Assignee: Bayer Aktiengesellschaft, Leverkusen, Fed. Rep. of Germany

[21] Appl. No.: 90,888

[22] Filed: Aug. 28, 1987

[30] Foreign Application Priority Data

Sep. 19, 1986 [DE] Fed. Rep. of Germany ....... 3631906

[51] Int. Cl.$^4$ ........................................... C07C 101/42
[52] U.S. Cl. ................................... 562/853; 562/433; 562/456; 562/861; 562/862; 562/863
[58] Field of Search ..................................... 260/544 D

[56] References Cited

FOREIGN PATENT DOCUMENTS 3142856 11/1983 Fed. Rep. of Germany ... 260/544 D

OTHER PUBLICATIONS

"Organic Reactions", vol. V, John Wiley & Sons, Inc., N.Y.

Primary Examiner—Paul J. Killos
Attorney, Agent, or Firm—Sprung Horn Kramer & Woods

[57] ABSTRACT

A process for the preparation of a compound of the formula

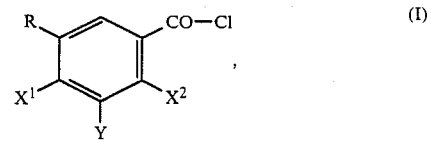

in which
  $X^1$ and $X^2$ each independently is chlorine or fluorine, and
  Y is chlorine, bromine, fluorine or iodine, comprising subjecting a compound of the formula

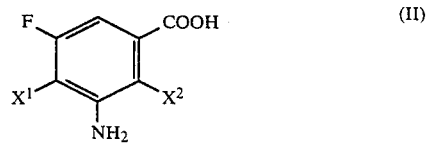

to a Sandmeyer or Balz-Schiemann reaction thereby to produce a carboxylic acid of the formula

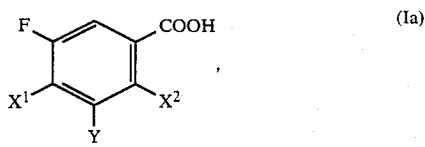

and converting the carboxylic acid (Ia) into an acyl chloride of the formula

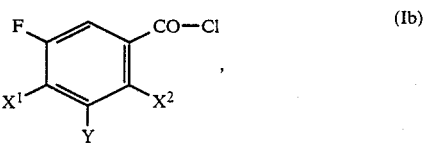

The compound (II) is new. The products are known intermediates for anti-bacterials.

4 Claims, No Drawings

PROCESS FOR THE PREPARATION OF BENZOIC ACID DERIVATIVES

The present invention relates to a process for the preparation of benzoic acid derivatives which represent valuable intermediates for the synthesis by the cycloaracylation process, of quinolonecarboxylic acids which have a very strong antibacterial action, as are described, for example, in the following patent applications: European patent application No. 126,355, German patent application No. 3,420,743 and European patent applications Nos. 183,129 and 184,035.

3-Chloro-2,4,5-trifluoro-benzoyl chloride can be prepared through chlorination of 2,4,5-trifluorobenzoic acid. A disadvantage of this process is that, during it, a mixture of nuclear-chlorinated benzoic acids is produced from which 3-chloro-2,4,5-trifluorobenzoic acid must be isolated by repeated recrystallization after work-up. After conversion into the acyl chloride, 3-chloro-2,4,5-trifluoro-benzoyl fluoride can subsequently also be prepared through a chlorine/fluorine exchange reaction (German patent application No. 3,420,796).

A further process describes the preparation of 3-chloro-2,4,5-trifluorobenzoyl chloride from 3-chloro-4-fluoro-aniline via an 11-stage process. A disadvantage is the inconvenient route, in which, in addition, some steps only proceed in poor yield (European patent application No. 183,129). An analogous process concerns the preparation of 3-bromo-2,4,5-trifluoro-benzoyl chloride (European patent applications Nos. 183,129 and 184,035). 2,3,4,5-Tetrafluorobenzoic acid is prepared from tetrachlorophthaloyl chloride (Zhurnal Obshchei Khimii 36, 139 [1966]), from tetrafluoroanthranilic acid (Bull. Chem. Soc. Jap. 45, 2909 [1972]) or from tetrafluorobenzene (Tetrahedron 23, 4719 [1967]; Z. Naturforsch. 31 B, 1667 [1976]), partly through complicated steps.

It has now been found that the compounds of the formula (I)

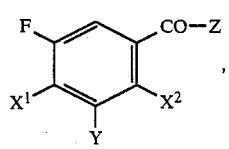

in which

X$^1$ and X$^2$ are identical or different and represent chlorine or fluorine,

Y represents chlorine, bromine, fluorine or iodine, and

Z represents hydroxyl, chlorine or fluorine, can be obtained by converting compounds of the formula (II)

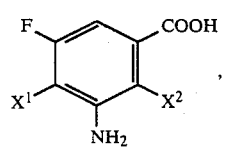

in which X$^1$ and X$^2$ have the abovementioned meaning, via a Sandmeyer or Balz-Schiemann reaction, into compounds of the formula (Ia)

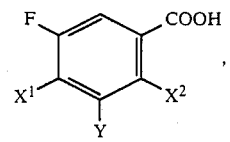

in which X$^1$, X$^2$ and Y have the abovementioned meaning, and, if appropriate, converting these carboxylic acids into an acyl chloride of the formula (Ib)

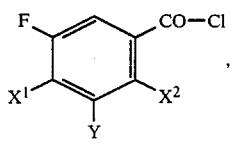

in which X$^1$, X$^2$ and Y have the abovementioned meaning, and, in the case where at least one of the radicals X$^1$ or X$^2$ represents chlorine, converting this, if appropriate through a fluorination reaction, via a compound of the formula (Ic)

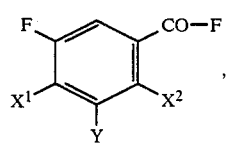

in which X$^1$, X$^2$ and Y have the abovementioned meaning, into a compound of the formula (Id)

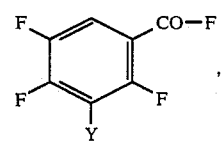

in which Y has the abovementioned meaning.

As an alternative to this, compounds of the formula (Ie)

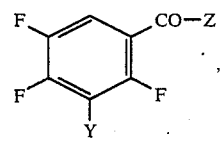

in which Y and Z have the abovementioned meaning, can be obtained by converting a compound of the formula (III)

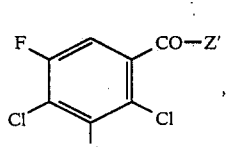

in which Z' can denote fluorine or chlorine, into 2,4,5-trifluoro-3-nitro-benzoyl fluoride of the formula (IV)

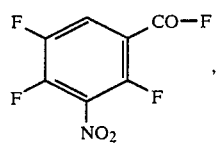  (IV)

saponifying this to form 2,4,5-trifluoro-3-nitro-benzoic acid of the formula (V)

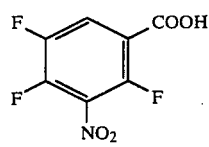  (V)

and then, after reducing the nitro group, converting (V), through a Sandmeyer or Balz-Schiemann reaction, into a compound of the formula (If)

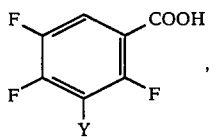  (If)

in which Y has the abovementioned meaning, and, if appropriate, converting this carboxylic acid of the formula (If) into a compound of the formula (Ig)

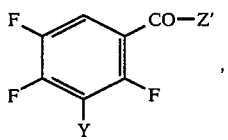  (Ig)

in which Y and Z' have the abovementioned meaning.

The advantage of the process according to the invention compared to known processes is that the selective reaction proceeds in few reaction steps from readily available precursors to form the desired intermediates. The compounds can thereby be prepared more economically.

The course of the reaction of the process according to the invention may be described, as an example, for the preparation of 3-chloro-2,4,5-trifluoro-benzoyl fluoride from 2,4-dichloro-5-fluorobenzoic acid by the following equation.

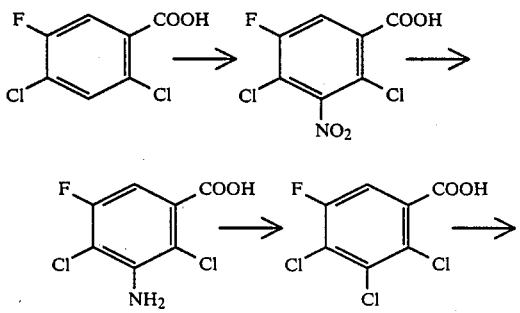

-continued

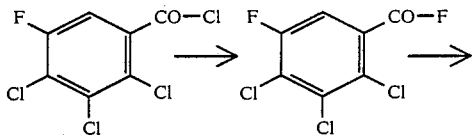

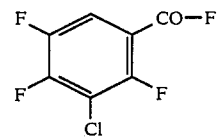

The 3-amino-2,4-dihalogeno-5-fluoro-benzoic acids of the formula (II) used as starting materials for the process according to the invention are new. They can be prepared by reducing 2,4-dihalogeno-5-fluoro-3-nitro-benzoic acids. Suitable reducing agents are, for example, iron, zinc, tin(II) chloride, sodium dithionite, lithium aluminum hydride or catalytically activated hydrogen in the presence of catalysts such as Raney nickel, Raney cobalt, platinum or palladium (see Houben-Weyl, Methoden der Organischen Chemie [Methods of Organic Chemistry], volume XI/1, page 341 [1957]). In order to prevent dehalogenation during the catalytic hydrogenation, it may be advisable to reduce the activity of the catalysts by adding a contact poison, for example sulphur compounds.

Suitable solvents are acetic acid, ethyl acetate, alcohols, such as methanol, ethanol, propanol or isopropanol, glycol monomethyl ether, tetrahydrofuran, dioxane, dimethylformamide, pyridine, acetone or water, or alternatively mixtures of these solvents.

The chemical reduction is carried out at temperatures from about 0° C. to about 120° C., preferably from about 20° C. to about 80° C., and at atmospheric pressure, and the catalytic reduction is carried out at temperatures from about 0° C. to about 60° C. and a pressure from about 1 to 30 bar, preferably at temperatures from about 0° to about 30° C. and a pressure of about 1 to 10 bar.

The conversion of the 3-amino-benzoic acids (II) and (V) into the tetrahalogenobenzoic acids (Ia) and (If) respectively proceeds through a Sandmeyer reaction if chlorine, bromine or iodine are to be introduced (see Houben-Weyl, Methoden der Organischen Chemie [Methods of Organic Chemistry], volume V/3, page 846 [1962], volume V/4, page 438, 641, [1960]) or through a Balz-Schiemann reaction if fluorine is to be introduced (see Houben-Weyl, Methoden der Organischen Chemie [Methods of Organic Chemistry], volume V/3, page 214 [1962]).

In the Sandmeyer reaction, the 3-amino-benzoic acid is diazotized in a mineral acid, such as sulphuric acid, hydrochloric acid or hydrobromic acid, by adding sodium nitrite at temperatures from about −10° C. to about +10° C., and the excess nitrous acid is eliminated by adding amidosulphonic acid or urea. The diazonium salt solution is decomposed into the corresponding chlorine, bromine or iodine compound by reaction with a solution of copper(I) chloride in concentrated hydrochloric acid, copper(I) bromide in concentrated hydrobromic acid or potassium iodide in water. The decomposition is initially carried out with the ice cooling and the mixture is then warmed to room temperature, and the reaction is completed, if appropriate, by increasing the temperature to about 80° C., until the nitrogen evolution ceases.

In the Balz-Schiemann reaction, the diazonium salt solution is converted, using tetrafluoroboric acid or sodium tetrafluoroborate, into the diazonium tetrafluoroborate, which can be thermally decomposed at about 80°–180° C., preferably at about 100°–150° C., into the corresponding 3-fluorobenzoic acid by dry decomposition, in a mixture with quartz sand or inert high-boiling solvents, such as, for example, chlorobenzene, toluene, xylene, ligroin or dioxane. The diazotization can alternatively be carried out in hydrofluoric acid at about 0°–10° C., and the reaction mixture is subsequently heated at about 50°–80° C. in an autoclave under pressure until nitrogen elimination occurs, or the thermal decomposition can alternatively be carried out after adding a suitable dipolar solvent, such as, for example, dimethyl sulphoxide.

The tetrahalogenobenzoic acids (Ia) or (If) are produced in these reactions as solids which can be reacted with a chlorinating agent, such as thionyl chloride, to form the tetrahalogenbenzoyl chlorides and, from these, with hydrogen fluoride to form the tetrahalogenobenzoyl fluorides.

The compounds (Id) can be prepared from the compounds (Ib) or the compound (IV) can be prepared from the compound (III) by fluorination with potassium fluoride.

The amount of potassium fluoride to be used depends on the number of chlorine atoms to be exchanged. For 1 chlorine atom, at least one mole of potassium fluoride is employed, but in general 1.1–1.5 moles are employed. At most, 2 moles of potassium fluoride are used per mole of chlorine; an amount of potassium fluoride in excess of this has virtually no influence on the degree of fluorination and the process becomes uneconomic. However, some of the expensive potassium fluoride can be saved if the benzoyl chloride (Ib) is previously fluorinated using hydrofluoric acid and the benzoyl fluoride (Ic), produced in high yield in this fluorination, is employed for the chlorine/fluorine exchange reaction with potassium fluoride. Due to the relatively high activation through the electronegative fluorocarbonyl group, the relatively high thermal stability of the latter, and the reduced amount of potassium chloride in the reaction mixture, this two-stage fluorination overall leads to an improved balance in the nuclear fluorination. By adding a catalyst, such as 18-crown-6, the yield can be further improved.

As solvents in the nuclear fluorination, the inert solvents which are known for fluorination reactions, for example dimethylformamide, dimethyl sulphoxide, N-methylpyrrolidone, diethyl sulphone and others may be used. However, tetramethylene sulphone (sulfolane) is particularly preferably employed.

The reaction temperature is between 160° and 260° C., depending on the desired degree of fluorination, but the reaction is preferably carried out at temperatures from about 180° C. to about 220° C.

The compounds prepared according to the invention are valuable intermediates for antibacterially active quinolonecarboxylic acids.

The following examples illustrate the invention.

EXAMPLE 1

2,3,4-Trichloro-5-fluoro-benzoic acid (a) 2,4-Dichloro-5-fluoro-3-nitro-benzoic acid 40 ml of concentrated nitric acid are added dropwise, with ice cooling and stirring, to 34 ml of concentrated sulphuric acid. 20.9 g of 2,4-dichloro-5-fluorobenzoic acid are added in portions to this nitration mixture, the temperature increasing to 45°–50° C. The mixture is then heated for a further 3 hours at 90°–100° C. and, after cooling to room temperature, poured into 350 ml of ice water, and the precipitate is filtered off under suction and washed with water. The moist crude product is dissolved in 30 ml of hot methanol, and 150 ml of $H_2O$ are added to the solution. The precipitate is filtered off under suction when cold, washed with $CH_3OH/H_2O$ and dried at 80° C. in vacuo. 21.2 g of crude 2,4-dichloro-5-fluoro-3-nitro-benzoic acid are obtained. It is sufficiently pure for the further reactions. Melting point: 192° C. (from toluene/petroleum ether).

(b) 3-Amino-2,4-dichloro-5-fluoro-benzoic acid 254 g (1 mol) of 2,4-dichloro-5-fluoro-3-nitrobenzoic acid are hydrogenated at 11°–20° C. and 10 bar of hydrogen in 1.8 liters of ethanol in the presence of 60 g of Raney nickel, and the reaction mixture is filtered and the filtrate is concentrated in vacuo. The pasty residue is kneaded with water, and the crystallized-out product is filtered off under suction, washed with water and dried.

Yield: 197 g (88% of theory)

Melting point: 175°–177° C., from toluene: 184°–187° C.

(c) 2,3,4-Trichloro-5-fluoro-benzoic acid

A. 86.1 g (0.38 mol) of 3-amino-2,4-dichloro-5-fluorobenzoic acid are dissolved in 1020 ml of 50% strength sulphuric acid at about 100° C. If appropriate, the solution is filtered through a glass frit, and immediately cooled in an ice bath with vigorous stirring. The suspension which precipitates out is diazotized at −5° C. to 0° C. by adding dropwise within 1 hour a solution of 33.8 g (0.49 mol) of sodium nitrite in 170 ml of water. 12.7 g of amidosulphonic acid are subsequently added in portions (foams vigorously) and the mixture is stirred for a further 15 minutes.

B. The solution A, cooled to −5° C. to 0° C., is added in portions from a separating funnel to a solution of 16.8 g (0.17 mol) of copper(I) chloride in 485 ml of 17% strength hydrochloric acid at −5° C. to −10° C. In order to break down the foam produced, the mixture is stirred vigorously and, if necessary, a little methylene chloride is added. The mixture is allowed to warm to room temperature within about 2 hours with stirring, and the solid product is filtered off under suction, washed with water and dried at 70° C. in a circulated-air cabinet.

Yield: 87 g (94% of theory)

Melting point: 157°–169° C., after recrystallization from toluene: 166°–170° C.

The product is further reacted without further purification.

EXAMPLE 2

2,3,4-Trichloro-5-fluoro-benzoyl chloride 737 g (3.02 mols) of 2,3,4-trichloro-5-fluorobenzoic acid are introduced into 1.5 liters of thionyl chloride at room temperature, and the mixture is refluxed for 16 hours until the gas evolution ceases. Excess thionyl chloride is removed by distillation, and the residue is distilled.

Yield: 694.6 g (87.8% of theory)
Boiling point: 100°–108° C./0.8–2 mbar
Purity: 98.5%.

EXAMPLE 3

2,3,4-Trichloro-5-fluoro-benzoyl fluoride 480 g (1.83 mols) of 2,3,4-trichloro-5-fluorobenzoyl chloride are introduced, with 240 g (12 mols) of hydrogen fluoride, at −5° to 0° C. into a stirred autoclave fitted with a pressure-control valve, the apparatus is pressure-sealed and warmed to 70° C. in steps, corresponding to the evolution of HCl. The hydrogen chloride produced is continuously released at 4–5 bar. When the evolution of HCl is complete, the mixture is cooled, the excess pressure is released and the reaction mixture is fractionated.

Yield: 413 g (92% of theory)
Boiling point: 114°–116° C./16 mbar, $n_D^{20}=1.5560$

EXAMPLE 4

3-Chloro-2,4,5-trifluoro-benzoyl fluoride 413 g (1.66 mols) of 2,3,4-trichloro-5-fluorobenzoyl fluoride are warmed to 180° C. for 6 hours with 392 g (6.76 mols) of potassium fluoride and 870 ml of dry sulfolane. The mixture is subsequently incipiently distilled (~145° C./20 mbar) in vacuo to the boiling point of sulfolane, and the crude distillate (362 g) obtained is refractionated.

Yield: 287 g (73.8% of theory)
Boiling point: 67° C./18 mbar, $n_D^{20}=1.4760$
Purity: 98.8%.

EXAMPLE 5

3-Bromo-2,4-dichloro-5-fluoro-benzoic acid

A. 50 g (0.22 mol) of 3-amino-2,4-dichloro-5-fluorobenzoic acid are diazotized, as described in Example 1c, in 600 ml of 50% strength sulphuric acid using 20 g (0.29 mol) of sodium nitrite in 100 ml of water.

B. The solution A is added dropwise, within about 50 minutes, at −10° C. to a solution of 15 g (0.1 mol) of copper(I) bromide in 200 ml of 48% strength aqueous hydrobromic acid with vigorous stirring, the reaction product precipitating after foaming up. In order to reduce the foam formation, 100 ml of methylene chloride are added, and stirring is continued without cooling. After 3 hours, the mixture is cooled and the precipitate is filtered off under suction, washed with water and dried at 70° C. in vacuo.

Yield: 58.3 g (92% of theory)
Melting point: 163°–169°; after recrystallization from toluene: 175°–178° C.

The crude product is adequately pure for the subsequent reaction.

EXAMPLE 6

3-Bromo-2,4-dichloro-5-fluoro-benzoyl chloride 58.3 g (0.2 mol) of 3-bromo-2,4-dichloro-5-fluorobenzoic acid are refluxed for 4 hours in 350 ml of thionyl chloride until the gas evolution ceases. Excess thionyl chloride is removed by distillation, and the residue is fractionated.

Yield: 43.7 g (70% of theory)
Boiling point: 108°–110° C./0.9–1.3 mbar
Purity: 98.2%.

EXAMPLE 7

3-Bromo-2,4,5-trifluoro-benzoyl fluoride 20 g (0.0653 mol) of 3-bromo-2,4-dichloro-5-fluorobenzoyl chloride, 17 g (0.3 mol) of potassium fluoride and 50 g of sulfolane are warmed to 150° C. for 22 hours in the presence of catalytic amounts (~20 mg) of 18-crown-6. The apparatus is subsequently evacuated, and the product is distilled to the boiling point of sulfolane (~145° C./20 mbar). The product is purified by redistilling the crude distillate (15 g, 86% purity).

Yield: 12.6 g (75% of theory)
Boiling point: 62° C./2 mbar
Purity: 94.4%.

EXAMPLE 8

2,4-Dichloro-5-fluoro-3-iodo-benzoic acid 11.2 g of 3-amino-2,4-dichloro-5-fluoro-benzoic acid are diazotized at 0°–5° C. in 30 ml of semiconcentrated hydrochloric acid by adding 20 ml of 2.5 molar sodium nitrite solution. Any excess nitrite present is destroyed by adding urea. An aqueous solution of 9.1 g of potassium iodide is added dropwise with ice cooling. When the addition is complete, the mixture is warmed to 70°–80° C. for one hour. The mixture is subsequently cooled, and the solid is isolated and recrystallized from toluene/petroleum ether (1:1).

Yield: 10.0 g (59.7% of theory)
Melting point: 185°–186° C.

EXAMPLE 9

2,4-Dichloro-5-fluoro-3-iodo-benzoyl chloride 10.0 g of 2,4-dichloro-5-fluoro-3-iodo-benzoic acid and 9.5 ml of thionyl chloride are boiled until gas is no longer produced. The remaining thionyl chloride is then stripped off in vacuo. 10.2 g of crude acyl chloride, which can be employed without further purification, remain.

EXAMPLE 10

A mixture of 35.3 g (0.1 mol) of 2,4-dichloro-5-fluoro-3-iodo-benzoyl chloride, 26 g (0.45 mol) of dry potassium fluoride and 20 mg of 18-crown-6 is heated at 90° C. for 15 hours in 67.5 g of dry solfolane. The mixture is subsequently stirred into an equal volume of water, and the organic phase is isolated and distilled. 4 g of a product mixture of boiling point 120°–130° C./20 mbar and the following composition are obtained:

5% of 2,4,5-trifluoro-3-iodo-benzoyl fluoride,
20% of 4(2)-chloro-2(4),5-difluoro-3-iodo-benzoyl fluoride,
4% of 2,4-dichloro-5-fluoro-3-iodo-benzoyl chluoride,
2% of 4(2)-chloro-2(4),5-difluoro-3-iodo-benzoic acid, and 67% of sulfolane.

EXAMPLE 11

2,4,5-Trifluoro-3-nitro-benzoyl fluoride (a) 2,4-Dichloro-5-fluoro-3-nitro-benzoyl chloride 254 g (1 mol) of 2,4-dichloro-5-fluoro-3-nitrobenzoic acid are refluxed in 700 ml of thionyl chloride with addition of 3 drops of dimethylformamide until the gas evolution ceases. Excess thionyl chloride is removed by distillation, and the residue is fractionated in vacuo.

Yield: 237.1 g (87% of theory)
Boiling point: 107°–115° C./0.5–0.7 mbar
Melting point: 40°–42° C.

(b) 2,4,5-Trifluoro-3-nitro-benzoyl fluoride 27.3 g (0.1 mol) of 2,4-dichloro-5-fluoro-3-nitrobenzoyl chloride are warmed at 100° C. for 24 hours with 24 g (0.44 mol) of dry potassium fluoride and 20 mg of 18-crown-6 in 68 g of dry sulfolane. The crude mixture is subsequently fractionated.

Yield: 5 g (purity: 81%; corresponding to 17% of theory)
Boiling point: 80°–90° C./mbar.

EXAMPLE 12

2,4,5-Trifluoro-3-nitro-benzoic acid 3.5 g (0.02 mol) of 2,4,5-trifluorobenzoic acid are introduced into a mixture of 6.8 ml of concentrated sulphuric acid and 8 ml of 98% strength nitric acid at 5°–10° C., and the mixture is then stirred without cooling. The temperature increases to 70° C. The mixture is heated for 5 hours at 80°–90° C., a further 8 ml of 98% strength nitric acid are added, and the mixture is heated at 80° C. for 2 hours. The mixture is then introduced into 100 ml of ice water, extracted thoroughly with dichloromethane, dried using sodium sulphate and concentrated. The oil remaining crystallizes. If is stirred with light petroleum, and the solid product is filtered off under suction and dried.

Yield: 0.5 g, melting point 106° C.

Mass spectrum: m/e 221 (M+), 204 (M+—OH), 191 (M+—NO), 158, 130, 30 (NO).

The corresponding amino derivative is obtained according to the process described in Example 1b).

It will be understood that the specification and examples are illustrative but not limitative of the present invention and that other embodiments within the spirit and scope of the invention will suggest themselves to those skilled in the art.

We claim:

1. A process for the preparation of a compound of the formula

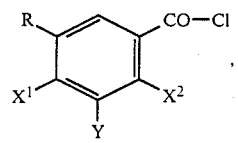

in which
  $X^1$ and $X^2$ each independently is chlorine or fluorine, and
  Y is chlorine, bromine, fluorine or iodine,
comprising subjecting a compound of the formula

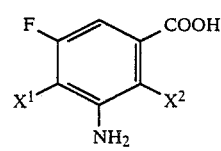

to a Sandmeyer reaction thereby to produce a carboxylic acid of the formula

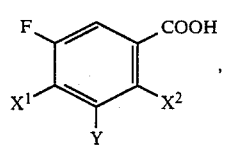

and reacting the carboxylic acid (Ia) with a chlorinating agent to produce an acyl chloride of the formula

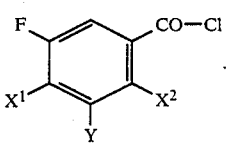

2. A process according to claim 1, wherein at least one of $X^1$ and $X^2$ is chlorine, the process including the further step of fluorinating (Ib) to produce the acid fluoride of the formula

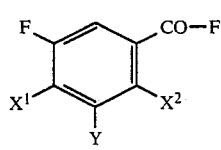

3. A process according to claim 1, wherein Y is fluorine.

4. A process according to claim 1, wherein Y is chlorine or bromine.

* * * * *

UNITED STATES PATENT AND TRADEMARK OFFICE
CERTIFICATE OF CORRECTION

PATENT NO. : 4,851,160

DATED : July 25, 1989

INVENTOR(S) : Petersen et al.

It is certified that error appears in the above-identified patent and that said Letters Patent is hereby corrected as shown below:

Title Page        ABSTRACT: Delete formula (I) " 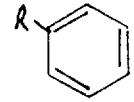 " and substitute -- 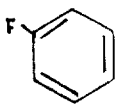 --

Col. 10, claim 1   Delete formula (I) " 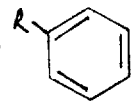 " and substitute
line 5

-- 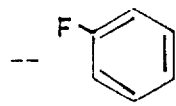 --

Signed and Sealed this

Twenty-eighth Day of April, 1992

Attest:

HARRY F. MANBECK, JR.

Attesting Officer      Commissioner of Patents and Trademarks